United States Patent [19]

Batt

[11] Patent Number: 5,294,537
[45] Date of Patent: Mar. 15, 1994

[54] MONOCLONAL ANTIBODY ASSAY FOR *LISTERIA MONOCYTOGENES*

[75] Inventor: Carl A. Batt, Groton, N.Y.

[73] Assignee: Cornell Research Foundation, Inc., Ithaca, N.Y.

[21] Appl. No.: 763,950

[22] Filed: Sep. 23, 1991

Related U.S. Application Data

[63] Continuation of Ser. No. 317,580, Mar. 1, 1989, abandoned.

[51] Int. Cl.$^5$ .................... G01N 33/569; C12N 5/18; C07K 15/28
[52] U.S. Cl. .................. 435/7.32; 435/7.92; 435/7.94; 435/7.95; 435/240.27; 530/388.4; 530/391.1; 530/391.3
[58] Field of Search ........... 435/7.32, 7.92, 7.94, 435/7.95, 70.21, 240.27, 968; 424/87; 530/388.4, 391.1, 391.3, 389.5, 387

[56] References Cited

U.S. PATENT DOCUMENTS 4,950,589  8/1990  Butman et al. .................. 435/7.32

OTHER PUBLICATIONS

Harlow et al, *Antibodies A Laboratory Manual* p. 372, Cold Spring Harbor Laboratory (1988).

Leinonen et al, Infect. Immun., 38(3):1203-1207 (Dec. 1982).

Voller et al, "Enzyme-Linked Immunosorbent Assay" in Manual of Clinical Laboratory Immunology pp. 99-109 (1986).

McLauchlin et al. J. Clin. Pathol. 41:983-988 (Sep. 1988).

Spitz et al, J. Immunol. Methods, 70:39-43 (1984).

Butman et al, Appl. Environ. Microbiol., 54(6) Jun. 1988) pp. 1564-1569.

Farber et al. J. Food Protection 50(6):479-484 (Jun. 1987).

*Primary Examiner*—Esther L. Kepplinger
*Assistant Examiner*—Carol E. Bidwell
*Attorney, Agent, or Firm*—Yahwak & Associates

[57] ABSTRACT

Mouse monoclonal antibodies which will specifically recognize the pathogen *Listeria monocytogenes* were produced by fusion of spleen cells from an animal immunized with live *L. monocytogenes* to an NS-1 myeloma partner, and three hybridomas were identified upon subsequent subcloning, Mab 20-10-2, Mab 36-6-12 and Mab 56-9-16 which were preferentially reactive with *L. monocytogenes* in a direct binding ELISA assay. An indirect "sandwich" assay was developed and used to further confirm the reactivity of these hybridomas using four serotypes of *L. monocytogenes* and other common cross reacting bacteria.

14 Claims, No Drawings

MONOCLONAL ANTIBODY ASSAY FOR *LISTERIA MONOCYTOGENES*

This is a continuation application of earlier application Ser. No. 07/317,580, filed Mar. 1, 1989, and now abandoned.

*Listeria monocytogenes* is a gram-positive non spore forming, motile bacillus first described in 1926. This organism is ubiquitous and has been isolated from milk and milk products, vegetables, raw meats, poultry, shellfish and other food products. The presence of *Listeria monocytogenes* in food products represents an ever increasing food safety problem particularly in infants and immunocompromised persons. Fatalities in symptomatic infected individuals within these groups may be as great as 40%.

Although there clearly exists a need for a reliable diagnostic procedure to identify this micro-organism in contaminated food products, the techniques currently available for the detection and enumeration of *L. monocytogenes* are not sufficiently rapid to assure the safety of the products prior to their consumption. These techniques are presently only useful in diagnosing the probable etiological agent following a suspected food illness outbreak. Current methodology for the detection and enumeration of Listeria involves enrichment in selective media including, in certain cases, incubation for a minimum of seven days at refrigeration temperatures. This is usually followed by a series of biochemical tests to confirm the micro-organism's identification as Listeria. The time required for final confirmation may exceed several weeks depending upon the initial population, the type of food and the co-contaminating microflora (Listeria species have been reported as cross-reactive to a wide number of other grampositive organisms). This protracted analysis time precludes the prescreening of a number of perishable, yet suspect products such as ready-to-eat foods and dairy products.

Since there is an antigenic cross reactivity between Listeria species and other gram-positive bacteria, any acceptable method for confirming the presence of these micro-organisms will require very specific antibodies if an immunodiagnostic approach is to be taken. To this end, it is believed any approach will require the use of homogenous (that is monoclonal) antibodies.

The fusion of mouse myeloma cells to spleen cells from immunized mice by Kohler and Milstein in 1975 (see Nature, 256:495) demonstrated for the first time that it was possible to obtain a continuous cell line producing monoclonal antibody.

Generally, in the production of monoclonal antibodies and the hybridomas making them, a convenient experimental animal, such as a mouse, is exposed to the antigen against which an antibody is desired. Typically, some of the antigen is injected into the animal, and its immune system is allowed to respond to it. This process may be repeated until the animal's immune system is presumed to be producing antibodies to the antigen, as well as such other antibodies as the animal may be producing without regard to the injections of the antigen. The animal is subsequently sacrificed, and antibody-producing cells (typically from the spleen) are isolated. Typically, a large number of such spleen cells are then fused with myeloma cells of the same species to obtain a hybrid cell colony which will reproduce without the self-limiting growth characteristics of most non-tumor cells. The fused cells are then cultured as cell lines of genetically identical, antibody-producing cells. However, there is no assurance that the antibody produced by any particular cell line is an antibody to the original antigen or that the antibody will be specific to the antigen. In order to select from among the many hybridoma cell lines thus created for a particular cell line that produces a desired antibody, it is necessary to screen the cell lines. This is done by testing the antibody produced by each cell line against the original antigen or a purified form thereof. The cell lines that are found by this means to produce the desired antibody are then preserved, and the remainder are discarded.

It should be emphasized that the unpredictable nature of hybrid cell preparation generally does not allow one to extrapolate from one antigen or cell system to another in order to predict precise outcomes of the application of conventional hybridization techniques. This unpredictability is further increased as the antigen is more complex and as an antibody is sought capable of recognizing the antigen in more than one species or in more than one form or context within a biological system.

Thus, while the general technique is well understood conceptually, there are many difficulties met and variations required for each specific case. In fact, there are no scientific assurances, prior to attempting to prepare a given hybridoma, that the desired hybridoma will be obtained, that it will produce antibody if obtained, or that the antibody so produced will have the desired specificity.

Within the past year both monoclonal antibodies and DNA probes have been reported which can detect Listeria. The DNA probes currently include a nucleotide sequence derived from the 16S ribosomal RNA of Listeria and a nucleotide sequence derived from a hemolysin gene isolated from *L. monocytogenes*. Both are currently being commercialized with the former already being marketed. One limitation of using DNA probes for routine monitoring of Listeria is the need for radioisotope labelling. DNA probes are only sensitive if labelled radioactively; the currently available nonradioactive DNA probes are not sufficiently sensitive. Given the need for a widely usable system, which can be performed in the food plant, radioactively labelled DNA probes are not generally acceptable. Therefore for all monitoring in plant in our opinion, it would seem a monoclonal antibody based system would be most feasible and suitable for detection of Listeria in food. A major effort is underway in a variety of laboratories to develop sensitive reliable nonisotopic labelling systems for DNA probes. Some success has been reported for nonisotopically labelled DNA probes to detect Salmonella.

The monoclonal antibodies presently being investigated include those which have been raised by direct immunization of mice using flagella from *L. monocytogenes* (Farber and Speirs, 1987). This antiflagellar monoclonal antibody does not appear to be absolutely specific for pathogenic Listeria so. and cross reacts with nonpathogenic strains.

A monoclonal antibody has been characterized which reacts with a heat stable antigen from Listeria. Although the exact nature of the antigen is not known, it has been commercialized and is available. It requires a preenrichment step after which the culture is collected and the extract produced by heating. The detection of this Listeria antigen is accomplished using an ELISA format and two different monoclonal antibodies to first capture the antigen and then subsequently detect the trapped antigen.

As the need for a rapid, organism specific test for Listeria is clearly needed, research was conducted to produce hybridoma cell lines providing monoclonal antibodies which specifically react with *L. monocytogenes* Scott A and its serotypes. Using these antibodies, an ELISA assay which tests for the presence of *L. monocytogenes* in contaminated food products was also developed. It is these hybridoma cell lines, the monoclonal antibodies produced therefrom, and the ELISA assay utilizing these monoclonal antibodies which comprise the subject matter of the present invention.

Hybridoma cell lines producing the monoclonal antibodies of the present invention have been deposited with, and accepted by, the American Type Culture Collection, Bethesda, Maryland and will be made available to the public during pendancy of any patent issuing therefrom in accordance with the Budapest Treaty. The monoclonal antibodies bear the following designations:

| Herein Designated | ATCC |
|---|---|
| 20-10-2 | HB 9947 |
| 36-6-12 | HB 9948 |
| 59-9-16 | HB 9949 |

Deposit is for the purpose of enablement only and is not intended to limit the scope of the present invention. Clones of these cell lines and other cell lines derived therefrom are considered to be foreseen by the present invention.

EXAMPLE I

Production of Monoclonal Antibodies

Five to seven week female Balb/c mice were immunized intrasplenically with $2.5 \times 10^3$ intact mid-logarithmic phase *L. monocytogenes* Scott A according to the method of Spitz et al., [J. Immunol. Methods 70:39–43 (1984)]. Eighty-eight hours after immunization, the animals were sacrificed, their spleens were removed, and splenic lymphocytes were fused with a murine plasmacytoma NS-1 using polyethylene glycol according to the method of Kohler et al., [Eur. J. Immunol. 6:292–295 (1976)], and plated in selective medium. Individual hybridomas secreting *L. monocytogenes* reactive antibodies as determined by recognized direct ELISA procedures were subcloned twice by limiting dilution. Large amounts of hybridoma supernatant and purified immunoglobulin was obtained by conventional affinity chromatography using a goat anti-mouse immunoglobulin conjugated to Sepharose column.

The antibody may be produced in larger amounts by growing the hybrid cell lines in a suitable culture medium such as ICM or RPMI (preferably serum free) or in vivo in a host such as a nude mouse. If desired, the antibody may be separated from the culture medium or body fluid, as the case may be, by conventional techniques such as ammonium sulfate precipitation, ion exchange chromatography, affinity chromatography, electrophoresis, microfiltration, and ultracentrifugation.

The monoclonal antibody may be used in conventional manual or automated screening tests to ascertain whether clinical samples (food, food products, or other samples from non-food sources) contain *Listeria monocytogenes*. These tests are based on the ability of the antibody to react selectively and involve incubating the sample in a container such as a tube or plate well with the antibody and observing the degree of reaction either visually or spectrometrically.

Labelled derivatives of the antibody may be made for use in a number of immunoassay techniques such as radioimmunoassay, fluorescence immunoassay or enzyme immunoassay. The labels that are used in making labeled versions of the antibody include moieties that may be detected directly, such as fluorochromes and radiolabels, as well as moieties, such as enzymes, that must be reacted or derivatized to be detected. Examples of such labels are $^{32}P$, $^{125}I$, $^{3}H$, $^{14}C$, fluorescein and its derivatives, rhodamine and its derivatives, dansyl, umbelliferone, luciferia, 2,3-dihydrophthalazinediones, horseradish peroxidase, alkaline phosphates, lysozyme, and glucose-6-phosphate dehydrogenase. The antibody may be tagged with such labels by known methods. For instance, coupling agents such as aldehydes, carbodiimides, dimaleimide, imidates, succinimides, bisdiazotized benzadine and the like may be used to tag the antibodies with the above-described fluorescent, chemiluminescent, and enzyme labels.

Tests using these labeled derivatives will involve incubating a clinical sample with the labeled antibody and detecting the presence or absence of labeled immune complexes on the cells in the sample via the label. The details of such procedures are well known in immunoassay art.

EXAMPLE II

Polyclonal Serum

Polyclonal antisera against *L. monocytogenes* was raised by intravenous immunization of female Flemish Giant rabbits at 3–5 day intervals for three weeks with formalin treated *L. monocytogenes*. The titer of this antiserum exceeds 1:25,600 in direct ELISA assays. This serum was partially purified by adsorption with *S. faecalis* according to conventional techniques.

EXAMPLE III

Direct Elisa

Hybridomas and purified antibodies were screened for anti-*L. monocytogenes* reactivity in a direct cell ELISA assay [J. Immunol. Methods 76:63-71 (1985)]. Poly-1-lysine was coated onto the wells of an Immulon I plate at 1 ug/ml. Next, test organisms including *Streptococcus faecalis*, non-pathogenic *Listeria ivanovii*, *Listeria seeligerii*, *Listeria innocua*, and the pathogen *L. monocytogenes* were added to the wells at $1.3 \times 10^5$ organisms/well and incubated overnight at 4° C. The plates were then centrifuged at 1000 rpm, 4° C., for 5 min. The wells of the plate were blocked with PBS containing 0.1% bovine serum albumin (BSA, fraction V) for 30 min., washed twice with PBS and then refilled with PBS-0.1% BSA. The plates were stored at 4° C until use. For assay, hybridoma supernatant or purified antibody was allowed to bind to the trapped bacteria for 2 hours at room temperature. The plates were washed once with PBS containing 1% Tween-20 and twice with PBS and 50 ul of anti-mouse Ig antibody conjugated to horseradish peroxidase was added to each well. Incubation proceeded for 2 hours at room temperature. The plates were washed and o-phenylenediamine was added to the wells and color development read at 405 nm.

EXAMPLE IV

Indirect Elisa

Immulon I plates were coated with an appropriate dilution of purified anti-*L. monocytogenes* antibody in 0.05% carbonate buffer (pH 9.6). After blocking with PBS containing 5% horse serum, 50 ul of ten fold dilutions of test organism in PBS containing 1% BSA and 0.05% Tween-20 was added to the wells and incubated for 2 hours at room temperature. For assays using milk, the test organisms were spiked into milk at an initial concentration of $1 \times 10^6$ organisms/ml and 150 ul added to well of a Immunion I plate coated with Mab 20-10-2. After incubation, the wells were washed as above and 50 ul of a 1/2000 dilution of anti-*L. monocytogenese* serum raised in rabbits was added. Incubation continued for 90 min. at room temperature. The amount of bound anti-*L. monocytogenes* was quantified by adding 50 ul of a 1/2000 dilution of anti-rabbit immunoglobulin serum conjugated to alkaline phosphatase and incubating for 90 min. at room temperature. The plates were then washed and 50 ul of p-nitrophenyl phosphate substrate added to the well. Color development was determined at 405 nm.

Table I lists the reactivity of the monoclonal antibodies, produced in accordance with the present invention, generated with the panel of test organisms. Of the 150 hybridomas tested, five, Mab 56, Mab 71, Mab 45-8, Mab 76-22 and Mab 20-10 reacted with all Listeria sp. tested (*L. ivanovii, L. seeligeri, L. innocua* and *L. monocytogenes*). All of the other antibodies generated reacted strongly with *L. monocytogenes*. Mab 20-10-2 was then screened against all serotypes of *L. monocytogenes*, but reacted selectively and to a lesser extent with other Listeria species tested. Six of the other antibodies generated Mab 49, Mab 76, Mab 59-9-16, Mab 36-6-12, Mab 20-10-2 and Mab 20-10-3 reacted most strongly with *L. monocytogenes* and weakly or not at all with the other Listeria species tested. None of the antibodies listed in reacted with a negative control test organism, *S. faecalis*.

TABLE I

Specificity of monoclonal antibodies in direct binding assay

| Mab | ivanovii | innocua | seelegerii | monocytogenes | S. faecalis |
|---|---|---|---|---|---|
| 73 | − | − | ++ | + | − |
| 49 | − | − | + | ++ | − |
| 56 | +++ | ++ | + | + | − |
| 59 | − | +++ | +++ | +++ | − |
| 71 | +++ | ++ | ++ | ++ | − |
| 76 | − | + | − | ++ | − |
| 45-8 | ++ | + | + | ++ | − |
| 76-1 | ++ | − | + | ++ | − |
| 76-22 | + | ++ | + | + | − |
| 76-23 | − | + | + | + | − |
| 59-9-16 | − | ± | − | ++ | − |
| 36-6-12 | − | − | ± | ++ | − |
| 20-10 | ++ | + | + | ++ | − |
| 20-10-2 | + | + | − | ++ | − |
| 29-10-3 | + | + | − | ++ | − |
| 20-10-8 | + | + | − | + | − |

Mab 20-10-2, which reacted with *L. monocytogenes* Scott A and weakly with *L. innocua* and *L. ivanovii* (Table I), was tested for its reactivity with other serotypes of *L. monocytogenes* (Table II).

TABLE II

Specificity of 20-10-2 for serotypes of *L. monocytogenes* using direct binding assay.

| *L. monocytogenes* serotype | Reactivity |
|---|---|
| Murray B | ++ |
| 1A Fac2, 3A Fac4 | ++ |
| 1A Fac2 | ++ |
| V37 | ++ |
| Scott A | ++ |
| 4AB Fac 6, 7.9 | ++ |
| 1971 5, 4b | ++ |
| *S. faecalis* | − |

As can be seen, Mab 20-10-2 reacted equally well with 5 other serotypes of *L. monocytogenes* tested. Again, it did not react with *S. faecalis*.

Preliminary attempts have been made to develop an indirect binding assay or "Sandwich ELISA" to further test the specificity of selected monoclonal antibodies. Initial assay formats using the polyclonal antiserum to trap the cells and subsequent detection using the monoclonal antibody proved unsatisfactory. As an alternative the monoclonal antibody was adsorbed to Immunion II plates and the trapped antigen detected using the adsorbed polyclonal antiserum. The secondary antibody was goat anti-rabbit conjugated to alkaline phosphatase. Plates were coated with Mab 20-10-2 overnight in .05M carbonate buffer, pH 9.6. The dilutions of the test bacteria were added to each well and incubated for 2 hrs. Polyclonal rabbit anti-*L. monocytogenes* serum (unadsorbed) was added for 90 min. The plates were washed and anti-rabbit IgG and IgM antibody conjugated to alkaline phosphatase.

The results typical of a number of assays are present in Table III.

TABLE III

Results of indirect ELISA using Mab 20-10-2 to trap antigen and unadsorbed rabbit polyclonal anti-Listeria serum for detection.

| | Number of organisms per well | | |
|---|---|---|---|
| Organism | $1 \times 10^5$ | $0.5 \times 10^5$ | $2.5 \times 10^4$ |
| *L. monocytogenes* | 1.006$^a$ | .103 | .731 |
| *L. ivanovii* | .159 | .135 | .072 |
| *L. innocua* | .218 | .000 | .163 |
| *L. seeligerii* | .112 | .000 | .081 |
| *S. faecalis* | .000 | .020 | .034 |

$^a$O.D. 405 nm

Although some inconsistencies appear, in general Mab 20-10-2 appears to specifically recognize *L. monocytogenes*. The inconsistencies observed are sporadic and appear to be a result of the assay format and not the monoclonal antibody used.

The same indirect assay format was used to further evaluate the specificity of Mab 59-9-16 and Mab 36-6-12 (Table IV).

TABLE IV

Results of indirect ELISA using Mab 59-9-16 or 36-6-12 to trap antigen and unadsorbed rabbit polyclonal anti-*L. monocytogenes* serum for detection.

| | 59-9-16[1] | 36-6-12[2] |
|---|---|---|
| *monocytogenes* Scott A | +++ | ++++ |
| *L. ivanovii* | ++ | + |
| *L. innocua* SH3V | ++ | + |
| *L. innocua* P5V5 | − | − |
| *L. innocua* | ++ | + |
| *L. seeligerii* | − | − |
| *S. faecalis* | − | − |
| *L. welshimeri* CF3VP | − | − |

TABLE IV-continued

Results of indirect ELISA using Mab 59-9-16 or 36-6-12 to trap antigen and unadsorbed rabbit polyclonal anti-*L. monocytogenes* serum for detection.

|  | 59-9-16[1] | 36-6-12[2] |
|---|---|---|
| *L. welshimeri* CCK9LG | − | − |
| Kurthia 10538 | − | ++ |

[1] 0.1 ug/ml Mab 59-9-12 on plate for trapping antigen
[2] 10.0 ug/ml Mab 36-6-12 on plate for trapping antigen The panel of test organism was extended to include *Listeria welshimeri* and Kurthia, an organism known to be immunologically cross-reactive with Listeria. Clearly, further refinement of the assay format is warranted. The utility of this indirect assay for the detection of *L. monocytogenes* in milk (Table V) was studied next.

TABLE V

Results of indirect ELISA using Mab 20-10-2 to detect *L. monocytogenes* in spiked milk samples.

| | Number of organisms per well | | |
|---|---|---|---|
| Organism | $2.5 \times 10^4$ | $1.3 \times 10^4$ | $7 \times 10^3$ |
| *L. monocytogenes* | .130[a] | .139 | .101 |
| *L. ivanovii* | .053 | .026 | .020 |
| *S. faecalis* | .018 | .053 | .035 |

[a] O.D. 405 nm

Test organisms were innoculated directly into milk at an initial concentration of $1 \times 10^6$/ml and 2 fold serial dilution of the spiked milk in buffer was added directly to plates coated with Mab 20-10-2. The results once again show some specificity for *L. monocytogenes*; the adsorption of *L. monocytogenes* to Mab 20-10-2 was two to three fold higher than that seen with *L. ivanovii* or *S. faecalis*. It should be noted that no preenrichment was used prior to assay.

In summary, the genus Listeria includes a number of species, however, it is increasingly clear that *L. monocytogenes* is the predominant (and perhaps only) pathogenic species found in food and food products. Accordingly, the selective detection of *L. monocytogenes* is of great importance since the ecology of Listeria is not well understood, and as the detection of Listeria sp. other than *L. monocytogenes* may not be an indicator of the food's safety. For this reason the purpose of the present invention has been to develop a monoclonal antibody which will specifically recognize *L. monocytogenes*, and in doing so, several of murine monoclonals produced by fusing spleen cells isolated from Balb/c mice immunized with *L. monocytogenes* to NS-1 plasmacytoma cells have been characterized. Hybridomas were screened by direct ELISA assay, and of the 150 hybridomas tested, six reacted most strongly with *L. monocytogenes* Scott A. The specificity of one of these antibodies, Mab 20-10-2, was further examined. Although Mab 20-10-2 reacted to some extent with *L. innocua* and *L. ivanovii* in the direct binding assay, greater specificity for *L. monocytogenes* was seen in the indirect ELISA assay. The antibody used on the solid phase specifically trapped *L. monocytogenes* as detected by a rabbit anti-mouse secondary antibody. In this assay format, little or no binding to the other Listeria species occurred. This difference in reactivity is not completely understood, however, it could be explained by differences in the presentation of the test organisms when adsorbed to plastic and when adsorbed by an antibody bound to plastic. Different antigenic epitopes on the bacteria may be exposed when the organisms is directly adsorbed to plastic. Additionally, the antibody may be binding non-specifically to the wells of the plate due to incomplete blocking of the poly-1-lysine originally bound to the wells to trap the test organisms. Differences in the charge of plastic adsorbed versus antibody adsorbed bacteria might also account for the different specificities of the direct and indirect ELISA assay. It is clear, however, that Mab 20-10-2 reacts with all serotypes of *L. monocytogenes* tested. Subsequent screening of one monoclonal, Mab 20-10-2 showed it to be reactive with all available *L. monocytogenes* serotypes (1-4) further demonstrating that it is species specific but not serotype dependent. Two others Mab 59-9-16 and 36-6-12 also show preferred specificity for *L. monocytogenes*.

There are a number of parameters to be optimized in order to increase the sensitivity and specificity of these monoclonal antibodies, however, these parameters can easily be optimized using conventional well-known techniques. In the indirect ELISA, for example, rabbit anti-*L. monocytogenes* polyclonal antiserum and a secondary goat-anti-rabbit antibody for detection. Greater specificity will probably be achieved using a cocktail of monoclonal antibodies for detecting *L. monocytogenes* trapped using a monoclonal antibody. Furthermore, the monoclonal antibodies used for detection of the trapped antigen preferably would be either directly conjugated to the reporter molecule or biotinylated to utilize the biotin-strepavidin amplification system. In addition to these modifications, the incubation conditions, buffers (ionic strength, pH) and other assay parameters could be manipulated to improve the assay. All of these modifications to the embodiment described herein are deemed to be within the purview of the present invention.

The above description was provided in order to explain best the principles and the practical applications of the subject invention thereby to enable those skilled in the art to utilize the invention in various other embodiments and various modifications as are suitable for the particular use contemplated. The foregoing description of the invention, therefore, have been presented only for purposes of description and illustration of the subject invention. It is not intended to be exhaustive or to limit the invention to the precise forms disclosed, and many modifications and variations thereof would become obvious to those skilled in the art from the teachings and disclosure herein and such changes and modifications are properly intended to be within the full range of equivalents of the following claims.

Having thus described my invention and the manner and process of making and using it in such full, clear, concise, and exact terms as to enable any person skilled in the art to which it pertains, or with which it is most clearly connected, to make and use the same, and having set forth the best modes for carrying out my invention.

I claim:

1. A monoclonal antibody that specifically binds to an antigenic determinant of *Listeria monocytogenes*, wherein the antibody is produced by a hybridoma cell line obtained from the fusion of a myeloma cell with a lymphocyte derived from a mouse previously inoculated intrasplenically with intact live *Listeria monocytogenes*, said hybridoma cell line selected from the group consisting of ATCC HB9947, ATCC HB9948, and ATCC HB9949.

2. A hybridoma producing a monoclonal antibody that specifically binds to *Listeria monocytogenes* selected from the group consisting of ATCC HB9947, ATCC HB9948, and ATCC HB9949.

3. A method of screening for the presence of *Listeria monocytogenese* in a clinical sample which comprises:
   providing a monoclonal antibody that specifically binds to *L. monocytogenes*, wherein the monoclonal antibody is produced by a phybridoma selected from the group consisting of ATCC HB9947, ATCC HB9948, and ATCC HB9949;
   contacting the monoclonal antibody with a clinical sample suspected of having *L. monocytogenes* therein;
   allowing the monoclonal antibody to specifically bind to any *L. monocytogenes* present in the sample to form an immune complex; and
   determining the presence or absence of the immune complex; wherein the presence of the immune complex is indicative of the presence of *L. monocytogenes* in the clinical sample.

4. A method according to claim 3 wherein the presence or absence of the immune complex is determined by:
   adding a second antibody that specifically binds to the immune complex, wherein the second antibody is conjugated to a fluorescent, radioactive or chromophoric label; and
   determining the presence of absence of the fluorescent, radioactive or chromophoric label.

5. A method according to claim 3 wherein the monoclonal antibody is adsorbed on a solid support.

6. A method according to claim 3 wherein any L. monocytogenes in the clinical sample is adsorbed onto a solid support that has been precoated with poly-L-lysine prior to contact with the clinical sample.

7. An immunoassay for screening for the presence or absence of *Listeria monocytogenes* in a clinical sample which comprises:
   providing a solid support having adsorbed thereon a monoclonal antibody that specifically binds to *L. monocytogenes*, wherein the monoclonal antibody is produced by a hybridoma selected from the group consisting of ATCC HB9947, ATCC HB9948, and ATCC HB9949;
   providing a clinical sample suspected of having *L. monocytogenes* present therein;
   contacting the solid support with the clinical sample;
   allowing the monoclonal antibody to specifically bind to any *L. monocytogenes* in the sample, thereby forming an immune complex on the solid support; and
   detecting the presence or absence of the immune complex on the solid support; wherein the presence of the immune complex on the solid support is indicative of the presence of *Listeria monocytogenes* in the clinical sample.

8. An immunoassay according to claim 7 wherein the presence or absence of the immune complex is determined by:
   contacting the solid support with a second antibody that specifically binds to the immune complex on the solid support, wherein the second antibody is conjugated with a fluorescent, radioactive or chromophoric label thereby forming a labelled complex on the solid support; and
   determining the presence or absence of the fluorescent, radioactive or chromophoric label bound to the solid support in the labelled complex.

9. An immunoassay according to claim 7 wherein the presence or absence of the immune complex on the solid support is detecting by:
   adding a second antibody that specifically binds to *L. monocytogenes*;
   allowing said second antibody to specifically bind with *L. monocytogenes* present in the immune complex on the solid support;
   adding a third antibody that specifically binds to the second antibody, wherein the third antibody is conjugated with a fluorescent, radioactive or chromophoric label thereby forming a labelled complex on the solid support and
   determining the presence or the absence of the label bound to the solid support in the labelled complex.

10. An immunoassay according to claim 7 wherein the second antibody is rabbit anti-*Listeria monocytogenes* antibody.

11. An immunoassay according to claim 7 wherein the second antibody is polyclonal.

12. An immunoassay according to claim 7 wherein the label is a chromophoric label.

13. An immunoassay according to claim 7 wherein the label is a fluorescent label.

14. An immunoassay according to claim 9 wherein the third antibody is conjugated with a radioactive label.

* * * * *